(12) United States Patent
Furia (10) Patent No.: US 7,959,573 B2
(45) Date of Patent: Jun. 14, 2011

(54) NEEDLE-GUIDE DEVICE, PARTICULARLY FOR ULTRASOUND PROBES

(75) Inventor: Roberto Furia, Genoa (IT)

(73) Assignee: ESAOTE, S.p.A., Milan (IT)

( * ) Notice: Subject to any disclaimer, the term of this patent is extended or adjusted under 35 U.S.C. 154(b) by 0 days.

(21) Appl. No.: 11/810,564

(22) Filed: Jun. 6, 2007

(65) Prior Publication Data

US 2007/0282205 A1 Dec. 6, 2007

Related U.S. Application Data

(62) Division of application No. 10/082,703, filed on Feb. 25, 2002, now Pat. No. 7,241,267.

(30) Foreign Application Priority Data

Mar. 5, 2001 (IT) .............................. SV2001A0008

(51) Int. Cl.
*A61B 8/00* (2006.01)

(52) U.S. Cl. ........ 600/461; 600/427; 600/459; 600/462; 600/411; 600/439; 606/182

(58) Field of Classification Search ................. 600/427, 600/459, 461, 411, 439, 462, 463, 466; 606/182
See application file for complete search history.

(56) References Cited

U.S. PATENT DOCUMENTS

| | | | | |
|---|---|---|---|---|
| 4,108,165 | A | | 8/1978 | Kopp et al. .................... 600/461 |
| 4,497,325 | A | * | 2/1985 | Wedel ........................... 600/567 |
| 4,542,747 | A | | 9/1985 | Zurinski et al. ............... 600/461 |
| 4,883,059 | A | | 11/1989 | Stedman et al. .............. 600/437 |
| 5,052,396 | A | * | 10/1991 | Wedel et al. .................. 600/461 |
| 5,427,108 | A | | 6/1995 | Bollinger ....................... 600/461 |
| 5,623,931 | A | | 4/1997 | Wung et al. ................... 600/461 |
| 5,758,650 | A | | 6/1998 | Miller et al. .................. 600/461 |
| 5,924,992 | A | | 7/1999 | Park et al. ..................... 600/461 |
| 5,941,889 | A | * | 8/1999 | Cermak ........................ 606/130 |
| 6,095,981 | A | | 8/2000 | McGahan ..................... 600/461 |
| 6,379,307 | B1 | | 4/2002 | Filly et al. ..................... 600/461 |
| 6,398,711 | B1 | * | 6/2002 | Green et al. ...................... 600/7 |

* cited by examiner

*Primary Examiner* — Brian Casler
*Assistant Examiner* — Joel M Lamprecht
(74) *Attorney, Agent, or Firm* — Woodard, Emhardt, Moriarty, McNett & Henry LLP (57) ABSTRACT

A needle-guide device, particularly for ultrasound probes, or the like, comprising a base body constructed and arranged for connection to the probe and at least one elongated guide hole for receiving a needle-like surgical tool, characterized in that said needle-guide device is made of at least two removably connectable parts, which are shaped in such a manner that each of them forms complementary parts of the peripheral delimiting wall of the elongated guide hole for the surgical tool, which peripheral wall parts complete each other when said two parts of the needle-guide device are connected, thereby forming an elongated guide hole for guiding the needle with a 360° covering delimiting wall.

15 Claims, 9 Drawing Sheets

NEEDLE-GUIDE DEVICE, PARTICULARLY FOR ULTRASOUND PROBES

CROSS-REFERENCES TO RELATED APPLICATIONS

The present application is a divisional patent application of U.S. patent application Ser. No. 10/082,703, filed Feb. 25, 2002, now U.S. Pat. No. 7,241,267, entitled "A Needle-Guide Device, Particularly for Ultrasound Probes" which is hereby incorporated by reference in its entirety. The parent patent application claims foreign priority benefits under 35 U.S.C. §119 to Italian patent application No. SV2001A000008, filed Mar. 5, 2001.

BACKGROUND OF THE INVENTION

The present invention relates to a needle-guide device, particularly for ultrasound probes, or the like, comprising a base body having means for connection to the probe and at least one elongated guide tube for an elongated, rodlike diagnostic or surgical tool, named needle.

Such devices are currently used to accurately guide diagnostic or therapeutic tools, such as needles for biopsy, thermoablation, alcoholization or localized injection of substances, especially of chemotherapeutic agents.

However, the word needle is used in the present description and in claims, to define any diagnostic or therapeutic tool for localized operation, which has a rodlike conformation, for at least a portion of its extension, for instance for a portion of a support stem of the tool.

Localized applications, such as biopsies, thermoablation or localized injection of therapeutic substances are currently performed in combination with imaging means, and particularly in combination with ultrasound probes. Ultrasonic imaging allows to see the needle, or at least one of the needles and the target region to safely orient and move the needle to the target point.

The needle/s are moved to their position by appropriately orienting the probe manually or mechanically and/or by sliding them inside a guide seat. Hence, the probe shall have a needle-guide for safely and stably accommodating the needle, thereby avoiding any mutual staggering and wrong positioning or insertion of the needle/s.

To this end, needle-guide devices such as the one described hereinbefore are known, which comprise an elongated cannula-shaped hole, or the like, wherein the needle is inserted.

These devices have the drawback of not allowing a sufficiently safe sterilization. In fact, hardly removable microbial residues may infiltrate in the elongated holes or cannulae. For this reason, single-use needle-guides of the above type are currently known, particularly made of plastic. However, this involves some drawbacks. Besides obvious cost drawbacks (considering that stable attachment of ultrasound probes often requires rather complex adaptations of the needle-guides, thereby involving rather high fabrication costs), material waste is caused, with a consequently higher environmental load and the materials in use do not often have a good stability, for instance to thermal action, which is a critical condition, in applications like thermoablation.

SUMMARY OF THE INVENTION

Therefore, the invention has the object of providing a needle-guide such as the one described hereinbefore which, by relatively inexpensive construction arrangements, allows to obviate the drawbacks of prior art needle-guides. Also, the invention has the object of improving needle-guides to achieve a better functionality with reference to the diagnostic and/or therapeutic techniques which use those tools.

The invention achieves the above purposes by providing a needle-guide as described hereinbefore, which is made of at least two removably connectable parts, which two parts are shaped in such a manner that each of them forms complementary parts of the peripheral delimiting wall of the elongated hole and/or cannula for the needle (3), which complete each other when said two parts of the needle-guide are connected, thereby forming an elongated hole for guiding the needle or a cannula with a 360° covering delimiting wall.

Particularly, the two needle-guide parts have mutual abutment surfaces which are tangent or secant to the elongated needle-guiding hole, whereas this hole is obtained by a combination of grooves which are formed either integrally on one of the mutual abutment surfaces of one of the two needle-guide parts or partly on one and partly on the other of the two abutment surfaces of both needle-guide parts.

The separation plane between the two needle-guide parts is parallel to the axis of the elongated hole and secant or substantially tangent to the hole.

The elongated needle-guiding hole may be provided with a section corresponding to the outer section of the needle, with the wall of the elongated hole adhering to the whole needle surface.

Possibly and advantageously, the elongated needle-guiding holes may also have polygonal, particularly square or rectangular sections, said square or rectangular sections having such a size as to be able to inscribe therein the cylindrical or elliptical or oval section of the needle. This provides the advantage of a wider range of position choices for the separation plane between the two needle-guide parts in the elongated hole area, there being no undercut situation if the separation plane intersects the hole with an orientation parallel to at least two sides thereof. Moreover, since the needle has to be held accurately as regards orientation but must be able to slide inside the hole in the direction of its axis, the use of rectangular or square holes limits the contact surfaces between the needle and the guide hole wall to individual tangent lines or bands, thereby obtaining a lower friction between the needle and the hole wall (friction force being also proportional to the contact surface) and an effective and safe hold of the needle in the oriented position.

According to an advantageous embodiment, the needle guide is composed of at least two removable parts, at least one base part and at least one second part, which two parts are separated from each other by a separation surface whose cross section is a broken rectangular curve, and forms a succession of alternate and parallel complementary engageable ribs, there being provided, in the opposite mutual abutment surfaces of the ribs of one or both of the two needle-guide parts, grooves having such a size and shape as to form together an elongated needle-guiding hole or cannula.

The broken rectangular line-shaped separation surface between said two needle-guide parts may have variable widths and generate guiding holes with different relative positions.

Obviously, the needle-guide may be divided in such a manner as to consist of more than two parts, for instance three parts, shaped in such a manner as to form complementary parts of the peripheral delimiting wall of the needle-guiding elongated hole or cannula.

Advantageously, in a preferred embodiment, the needle-guide is composed of a base for connection to the ultrasound probe, which has at least one longitudinal groove, for engaging longitudinally continuous or discontinuous extensions of the side walls of a longitudinal groove provided in the other needle-guide part. Here, the bottom of the longitudinal groove in the base forms the complementary part for completing the elongated hole or cannula, whose other peripheral walls consist of the bottom of the longitudinal groove of the other needle-guide part, of the side walls of said groove and of the extensions of said side walls of the groove in the second part of the needle-guide.

By this arrangement, at least but not only in the disassembled condition, the elongated hole is longitudinally completely open, whereby it may be cleaned and sterilized with the highest safety but, unlike the case of the separation plane secant to the elongated hole or cannula and parallel to the longitudinal axis thereof, a perfect mutual centering effect between the two needle-guide parts is ensured, as well as a stable hold of said proper position with reference to transverse staggering.

Obviously, alternatively to the above, instead of two extensions of the side walls of the longitudinal grooves of the second needle-guide part, the second needle-guide part may be arranged to have a single extension of one of the two side walls of the longitudinal groove, whereas the other extension may be provided on the base part, as an extension of the opposite side wall of the longitudinal groove in the base part of the needle-guide. Here, each of the two parts of the needle-guide forms two of the opposite walls of the elongated hole or cannula.

The arrangement of the extensions of the side walls of the grooves in the two parts of the needle-guide may be also alternate and complementary over the length of the two extensions in the longitudinal direction of the grooves, either on one side and along the two opposite sides.

The second part of the needle-guide may be stably and removably secured to the needle-guide base in any manner, and particularly by means of screw-threaded devices, such as fastening bolts, or the like. In a particularly advantageous embodiment, one of the parts of the needle-guide, particularly the base part, has a wall parallel to the connecting direction, i.e. perpendicular to the separation plane, which has a recess for accommodating a fastening bolt which is screwed into a threaded hole formed in the other part, in an adjacent wall, adhering against said wall of the first part of the needle-guide. Alternatively to using bolts, said second part of the needle-guide may have a threaded pin of such a length as to project beyond the wall of the first part, through the recess provided in said wall and onto which threaded pin a nut screw is tightened.

Alternatively, the two mutually adhering walls of said two parts of the needle-guide may have, the inner one, a threaded hole and the other one a through hole, a threaded bolt with a tightening head being provided to fasten said two walls together.

According to an additional characteristic, the needle-guide may have a slender or tapering head, particularly having rounded edges, especially being wedge-shaped.

As a whole, the needle-guide may have a shape tapering toward the front end, especially a wedge shape. This is particularly advantageous in combinations of the above needle-guide with endocavitary probes, such as for uterine biopsy applications or the like.

In order to limit the presence of discontinuities, which might cause damages or pain to the patient, the front head, also perforated, is arranged to be a single piece, and preferably made of one piece with the base part of the needle-guide.

In this case, the through hole in said head part is widened on at least one side or for a portion of its inner delimiting surface, the second part of the needle-guide being provided, on its end side, with a wall extension which may be axially fitted in the through hole of the front head, coinciding with said wider portion and complementary thereto so as to complete, even in the front head of the needle-guide, the delimiting wall of the elongated through hole.

Advantageously, the second part of the needle-guide has said extensions on two opposite sides and in the form of front extension wings of the two side walls of the groove provided in said second part of the needle-guide, whereas the front head of the needle-guide has complementary widened portions in the corresponding walls.

In a further improvement, the bottom wall of the groove of the second needle-guide part also has an extension wing, the front head of the needle-guide being arranged to be accordingly widened even in the area of said extension wing of the bottom side of the groove of the second needle-guide part.

The extension wings of the side and/or bottom walls of the groove in the second part of the needle-guide are thinner than the wall of the second part of the needle-guide and than the head of the needle-guide, whereby an abutment step is formed between the front end of the second part of the needle-guide and the facing rear end side of the front head.

In accordance with an additional advantageous characteristic, the front head of the needle-guide, which is integral with the base part of the needle-guide, has a through aperture which communicates with the elongated hole provided therein at least one of the sides of said head, preferably at one of the two transverse sides, not coinciding with the extension wings of the second part of the needle-guide and particularly at the side of the base part of the needle-guide which is opposite the second part of the needle-guide and meant to adhere against or turned toward the probe, whereas in the front head, the needle is only substantially guided on three sides and through less than 360° at least in coincidence with the through aperture.

Advantageously, the front head of the needle-guide is relatively short as compared with the length of the rest of the needle-guide, in which the elongated hole or cannula have a continuous delimiting surface.

According to a further improvement, the front head of the needle-guide has a steeper tapered front end than the remaining portion of said head on the side connected to the second part of the needle-guide, whereas in said end portion and in the wall opposite the one with the aperture, the needle projection opening is provided, which takes an elongated shape, and in said end, the elongated hole delimiting walls are continuous and made of one piece, as well as directly accessible from the entry aperture.

Particularly, said front end of the front head of the needle-guide still has a needle guiding surface on the aperture side opposite to the one wherein the second part of the needle-guide fits, which surface extends from the front end of said aperture to the front apex of the front head.

As stated above, the needle-guide is designed to be mounted on an ultrasound probe, wherefore the invention also relates to a combination of a needle-guide and an ultrasound probe, wherein the base of the needle-guide is removably attachable to the probe body in a stable and predetermined position, said base having one or more shape mating extensions which adhere to a portion of the outer surface of the ultrasound probe body and/or mutual interlock engagement means, as well as clamping means.

In one embodiment, the needle-guide as described herein, having a tapered front head is designed to be connected to an endocavitary probe, which typically has a substantially cylindrical or other similar shape, also being elongated and having a rounded head, the base of the needle-guide having a surface whereby it rests on the probe case only in a few partial portions of the longitudinal extension and particularly in the end portions of the base of the needle-guide.

Further, the facing surfaces of the base of the needle-guide and of the probe case have complementary centering projections and recesses arranged over their length.

According to an improvement, the probe case may have recesses for accommodating supporting feet or extensions of the base of the needle-guide, provided at least at the ends thereof.

Particularly, the front head of the needle-guide has a front engagement extension on the side turned toward the probe case, which is designed to engage in a recess of the probe case, in such a manner that the tapered end of said front head can be connected thereto without forming outer steps or discontinuities.

In this case, since the centering pins and the means for engaging the front head of the needle-guide to the probe are effective position-holding means for the base of the needle-guide, the needle-guide is removably secured to the probe by means of a clamping collar provided at the rear end portion of the needle-guide.

An additional embodiment of the needle-guide combined with an external ultrasound probe having a bulged shape and a wider head as compared with the handgrip, has a base with two front extensions for resting on preferably symmetrically coincident front widened portions of the bulged shape, and an extension with a fastening screw which overlaps the rear side of the widened head against which the fastening screw is tightened. The fastening action so obtained is substantially concentrated in three points and is highly stable.

According to a further improvement, the needle-guide may have two, three or more elongated holes or two, three or more elongated guiding cannulae which are arranged in such a manner as to bring at least one of the needles in an ultrasound probe imaging position, whereas the other needle/s have predetermined and fixed positions relative to the former.

Hence a proper guiding action of the needle set is obtained, and the target area may be widened, for instance for a thermoablation application or for a localized injection of substances.

Advantageously, the invention proposes that this needle-guide type is also composed of two parts, a separation plane or surface being provided between the at least two parts, which is parallel to the axis of the corresponding elongated hole or cannula, and is secant or at least tangent to the corresponding hole, so that, by the separation between said at least two parts, all the elongated holes or cannulae are longitudinally open on at least one portion of a side.

Here again combinations of grooves and walls may be provided in said two parts which, by their mutual engagement, simultaneously form the complementary parts of the delimiting surfaces of the two, three or more holes in the needle-guide.

In an advantageous embodiment which includes three needle guiding elongated holes or cannulae and in which the needle-guide is divided into a base and a second part to be removably fastened to the base, the base of the needle-guide has a groove which accommodates the second part of the needle-guide, and has longitudinal side walls and a bottom wall, whereas an additional narrower groove is provided in the middle of the bottom wall and in turn has an additional groove in its bottom wall, which forms two longitudinal side walls and a longitudinal bottom wall for guiding the needle, whereas the second part of the needle-guide has, on the surface turned toward the bottom of the housing groove, a longitudinal median rib which coincides with the narrower longitudinal median groove in the base part and forms the missing needle guiding surface, completing the surfaces provided in the third groove, whereas, in the surfaces of the second part of the needle-guide, on the two sides of the longitudinal medial rib, longitudinal grooves are provided which form, with the facing surfaces of the first groove for accommodating the base part, at the two sides of the median groove, the delimiting surfaces of the two additional needle guiding elongated holes.

The advantages of the present invention are self-evident from the above description. The needle-guide device may be easily disassembled and allows to access the guiding elongated holes for a complete and safe sterilization. This allows to manufacture reusable needle-guides, from metal materials which do not involve drawbacks in various applications.

The needle-guide of the invention perfectly fits any application, as proven by the application embodiments to both endocavitary and external probes.

It shall further be noted that the individually described characteristics may be provided in any combination, even regardless of the individual specific embodiments.

The invention relates to further improvements which will form the subject of the appended claims.

BRIEF SUMMARY

A needle-guide device, particularly for ultrasound probes, according to one embodiment of the present invention comprises a base body having means for connection to an ultrasound probe and at least one elongated guide tube for an elongated, rodlike diagnostic tool characterized in that the needle-guide is made of at least two removably connectable parts which are shaped in such a manner that each of them forms complementary parts of a peripheral delimiting wall of an elongated hole for cannula for the needle which peripheral wall parts complete each other when the two parts of the needle-guide are connected, thereby forming the elongated hole for guiding the needle (or cannula) with a 360 degree covering delimiting wall.

A needle-guide device, particularly for ultrasound probes, according to another embodiment of the present invention comprises a base body constructed and arranged for connection to a probe and at least one elongated guide tube for an elongated, rodlike diagnostic tool, characterized in that the needle-guide device has a plurality of elongated holes or a plurality of cannulae for guiding a plurality of needles or rod-like tools which are arranged with their axes coincident with a single plane or having axes arranged on more than one plane, particularly having hole axes arranged at the vertices of ideal polygonal elements, such as triangles, quadrilaterals, or the like, or in any other different mutual arrangement.

A combination of a needle-guide device and an ultrasound probe according to another embodiment of the present invention comprises a hand grip portion characterized in that a base of the needle-guide is removably attachable to a body portion of the probe in a stable and predetermined position, the base having one or more shape mating extensions which adhere to a portion of the outer surface of the ultrasound probe body and mutual interlock engagement features and clamping means.

One object of the present invention is to provide an improved needle-guide device for an ultrasound probe as well as a needle guide device in combination with an ultrasound probe.

Related objects and advantages of the present invention will be apparent from the following description.

DETAILED DESCRIPTION

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Figure 1:
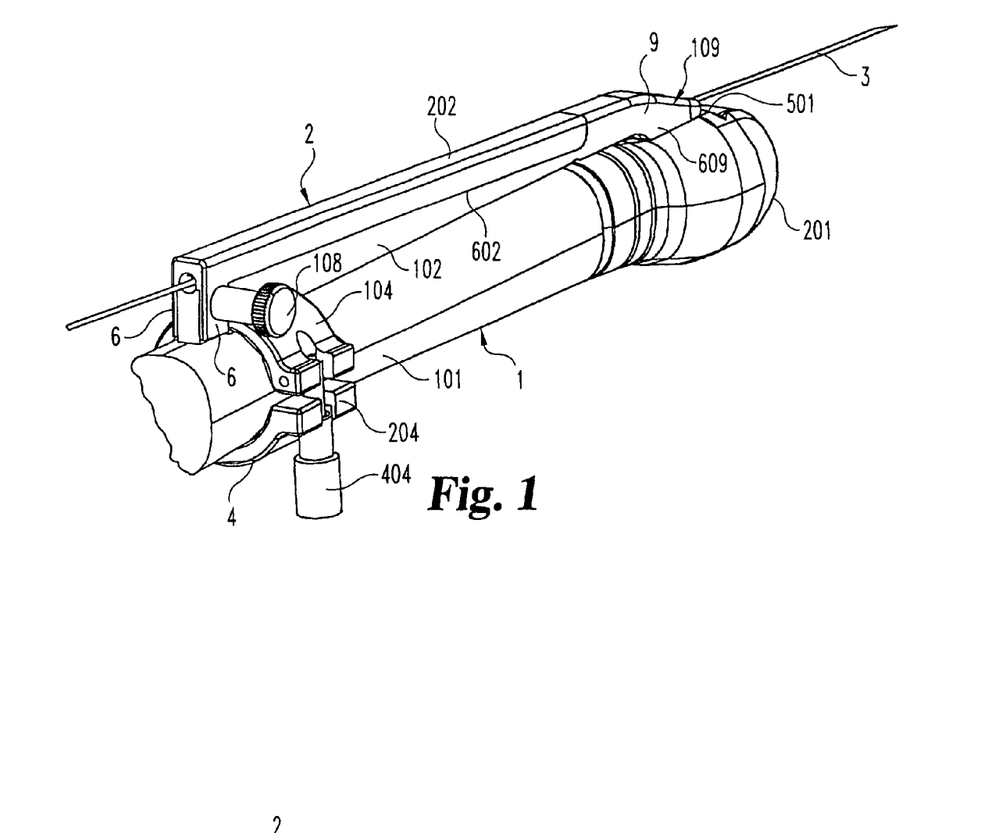
FIG. 1 is a perspective view of the rear side of an endocavitary ultrasound probe, whereto a needle-guide according to a first embodiment of the invention is connected.
Figure 2:
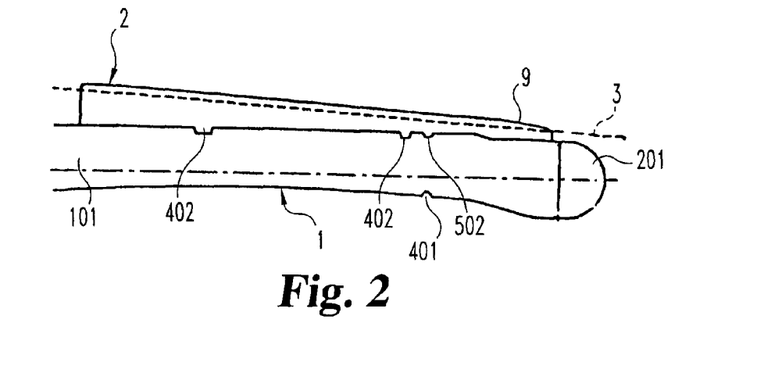
FIG. 2 is a sectional view of a detail of the probe as shown in FIG. 1, with a needle-guide as shown in FIG. 1 connected thereto.
Figure 3:
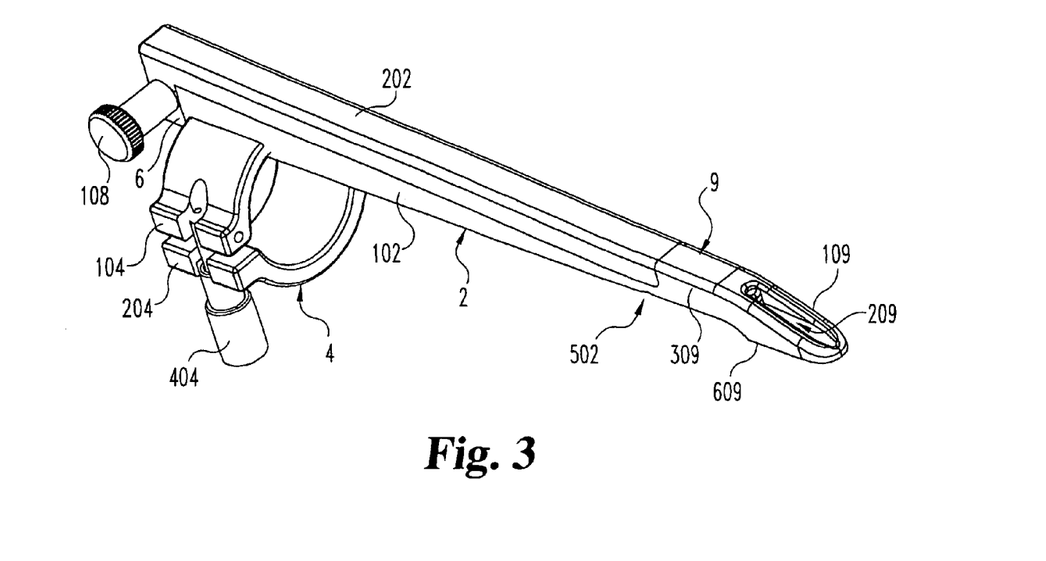
FIG. 3 is a perspective view of the needle-guide only, as shown in the previous Figures, and as seen from the front side.
Figure 4:
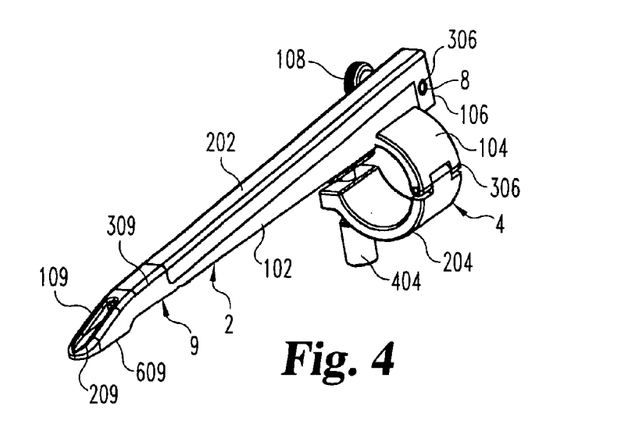
FIG. 4 is a perspective view of the needle-guide as shown in FIG. 3, and as seen from the other side.
Figure 5:
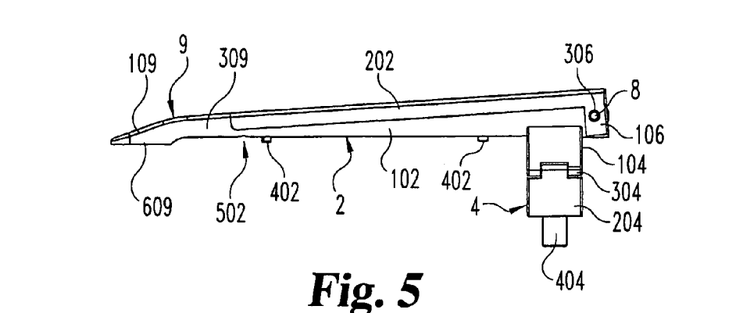
FIG. 5 is a side elevational view of the FIG. 3 needle-guide.
Figure 6:
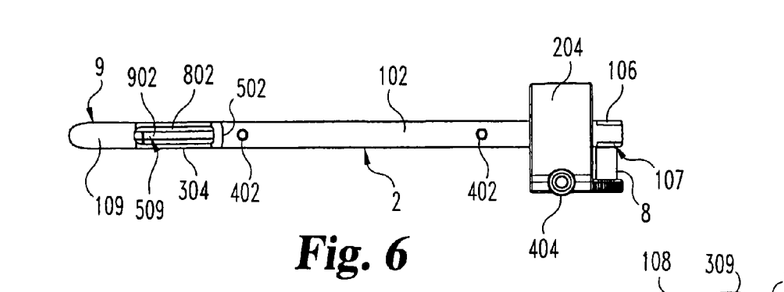
FIG. 6 is a bottom plan view of the FIG. 3 needle-guide.
Figure 7:
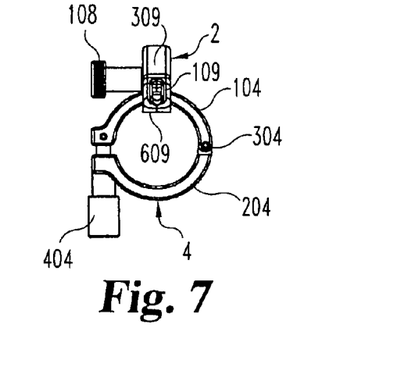
FIG. 7 is a rear elevational view of the FIG. 3 needle-guide.
Figure 8:
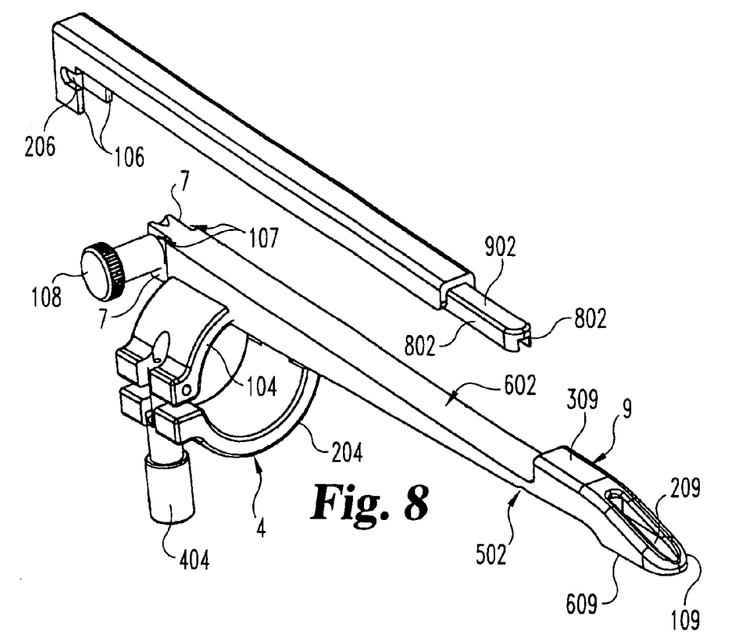
FIG. 8 is a perspective view like that of FIG. 3, in which the two parts of the needle-guide are shown separately, in exploded view form.
Figure 9:
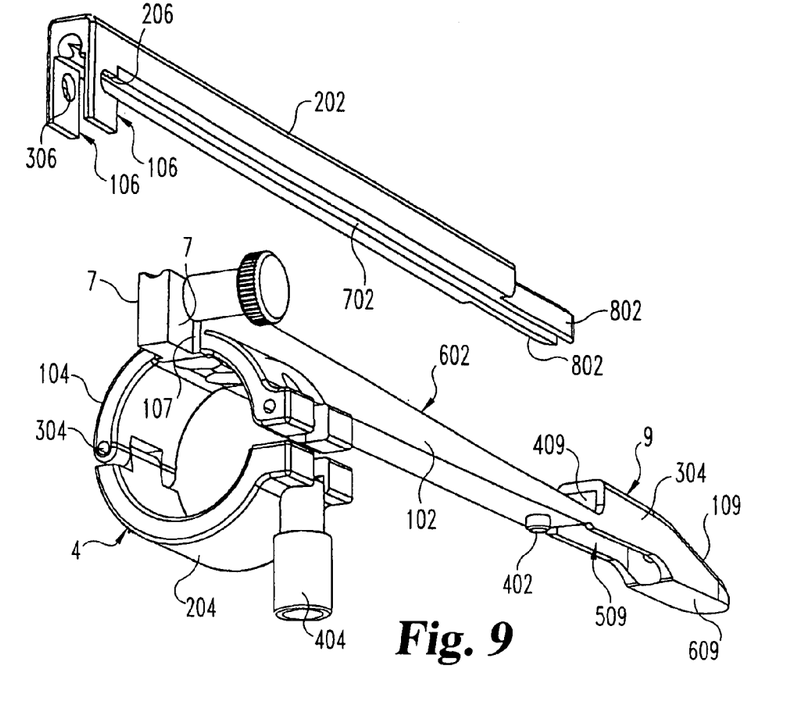
FIG. 9 is a perspective view of the rear side of the two parts of the needle-guide, shown in FIG. 8.
Figure 10:
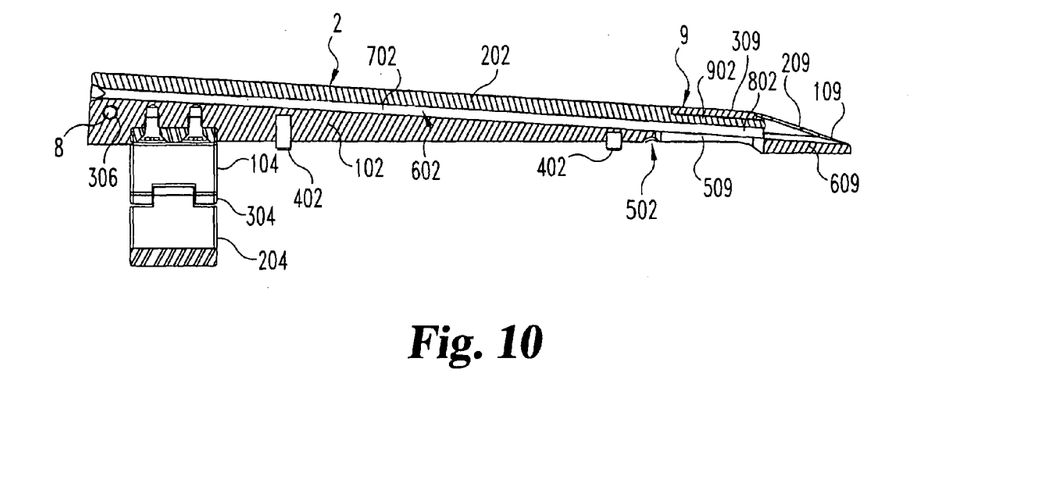
FIG. 10 is a sectional view as seen through a median plane passing through the axis of the needle and/or of the elongated guiding hole.

Referring to FIGS. 1 to 10, the invention is shown in the form of a combination of a needle-guide 2 and an endocavitary probe 1. The probe 1 has a substantially cylindrical shape with a handgrip portion 101 and a head 201 which contains the ultrasonic pulse emitting and receiving transducers.

The needle-guide 2 has an elongated shape with a wedge-shaped profile tapering from back to front and is composed of two connectable and separable and removably fastenable parts 102, 202, i.e. a base part 102 and a second part 202. The two parts define an elongated through hole which extends all along the needle-guide 2 from the rear end to the front head 9 thereof. The elongated hole is designed to accommodate a rodlike tool 3 for diagnostic or therapeutic applications, particularly a biopsy needle, a thermoablation needle, or a needle for injecting chemotherapeutic agents, or the like. The elongated hole has such a size, as related to the diameter of the needle 3 as to be able to hold the needle 3 in the proper position and to allow it to be axially displaced inside the needle-guide 2.

The needle-guide 2 is disposed with its longitudinal axis having the same front-to-back orientation as the needle in relation to the probe, in the front-to-back direction of the probe 1. Also, the elongated hole for guiding the needle 3 has such an inclination as related to the axis of the probe 1, that the front end of the needle falls within the target scan area of the probe 1 to be imaged during use.

Advantageously, the inclination of the hole for guiding the needle 3 substantially corresponds to the inclination of the free inclined end of the second needle-guide part 202. This provides a visual impression of needle inclination and facilitates the fabrication of the second needle-guide part.

The base 102 of the needle-guide has a clamping collar 4 at the rear end (with reference to the head 201 of the probe 1), one half 104 thereof being integral with said base 102, whereas the other half 204 of the collar 4 is hinged by hinge 304 to an end of said first half 104, and the two opposite free ends of the halves 104, 204 may be clamped together by screw threaded means 404 in a manner which is typical for clamping collars.

On the lower side resting on the probe 1, the base 102 has means 402, 502 for centering and positioning it on the probe, consisting of ridges or pins which cooperate with coincident recesses or notches 401 formed on the outer body of the probe 1. Possibly, the centering means 402, 502 have such a height as to keep the side of the base 102 turned toward the probe case slightly raised therefrom.

The base 102 has a surface 602 for supporting the second part 202 of the needle-guide, whereas the second part 202 of the needle-guide has a central groove 702 which is open toward said support surface 602. The second part 202 of the needle-guide has tapered extensions 802, 902 of the delimiting walls of the groove 702 at its front end. The extensions 802, 902 are externally tapered and extend flush with the inner delimiting sides of the groove 702, while forming an outer step 5 with the end side of the second part 202 of the needle-guide.

The second part 202 of the needle-guide has, at its rear side, two lateral lower wings 6, which rest on the two appropriately recessed corresponding opposite sides 7 of the rear side of the base 102. The lateral lower wings 6 and the rear recesses 7 have facing end sides 106, 107 which form axial abutment surfaces for the needle between the two needle-guide parts 102, 202.

In one of the two lateral recessing surfaces 7 of the base part 102, a threaded hole is provided into which a threaded pin 8 with a tightening head is screwed. The corresponding wing 6 of the second part 202 of the needle-guide 2 has a recess 206 open on the side turned toward the front end of the needle-guide 2 and coincident with the threaded hole, in which the threaded pin 8 is engaged, thereby allowing the two parts of the needle-guide 2 to be mutually clamped. In accordance with an improvement, the threaded hole for the threaded pin 8 is a through hole and the opposite wing 6 of the second part 202 of the needle-guide also has a coincident hole for engaging the end of the threaded pin 8. The latter is of such a length that, in the clamped position, it is engaged in the hole 306 of the wing 6 without projecting therefrom, and also remains partly engaged in said hole 306 in an incomplete clamping position of the threaded pin 8.

The base part 102 of the needle-guide 2 has a front head at the front end, which is made of one piece therewith. The head 9 has a steeper front portion 109, in which a projection opening 209 for the needle 3 is provided, which takes a slot-like shape due to inclination. The steeper portion 109 is followed by a portion 309 having an inclination corresponding to that of the second part 202 of the needle-guide when it is mounted on the base 102. This portion 309 has substantially the same length as the extensions 802, 902 of the walls of the groove 702 in the second part 202 of the needle-guide. The front head 9 has a hole 409 for engaging said extensions, whose internal shape is complementary to the external shape of the extensions, whereas the end edge of the second part 202 of the needle-guide 2 forms a shoulder for abutment against the rear end side of the front head 9 and is connected thereto for a substantially flush completion thereof.

A slot-like aperture 509 is provided on the front head side 9 turned toward the probe 1 and lying over the open side of the extension of the groove 702, coincident with said extension, which aperture extends transversely all along the engagement hole 409 of the front head 9. At the more tapered end 109 of the front head 9, the side turned toward the probe 1 is closed and is completely accessible from the needle projection hole which, due to the inclination in the corresponding side has the shape of a slot. Further, at said end side 109, the front head 9 has an extension 609 toward the probe 1 which is designed to be engaged in a complementary recess 501 formed in the case of the probe 1. The depth of the recess and the profile of the probe and of the front portion 109 of the head 9 of the needle-guide are such that, in the assembled position, the steeper front side 109 of said front head is joined to the outer surface of the case of the probe 1 substantially without forming any step therewith, and being connected therewith in a substantially harmonic manner.

In the embodiment as shown in the Figures, the separation plane between the two parts 102, 202 of the needle-guide 2 is substantially tangent to the lower side of the hole for guiding the needle 3, which is formed by the side for supporting the second part 202 of the needle-guide 2 on the base part 102 of the needle-guide 2. This plane may be also arranged to be secant to the position of the elongated hole for guiding the needle 3, and in this case, a portion of the groove 702 must be obviously also provided in the surface of the base part 102 against which the second part 202 rests.

Moreover, in this embodiment, the mutual position of the two needle-guide parts is maintained by complementary engagement means transverse to the needle axis, on the rear side of the needle-guide, from the end engagement between the two needle-guide parts to the front end.

According to a possible variant, which will be explained more clearly in the description of the next embodiment, the separation plane between the two needle-guide parts may also have a square wave profile, as related to the cross section of the needle-guide.

Here, for example, extensions may be provided not only for the front end of the second part 202 of the needle-guide 2, but also for the side walls of the groove 702, in this case forming ribs which project on both sides of the groove, toward the surface resting on the base 102 of the needle-guide 2. The base may have a groove of such a width and depth as to accommodate in a substantially accurate manner the two ribs extending from the side walls of the groove 702, which form the bottom of the groove in the base 102, and the wall for completing and/or closing the elongated needle guiding hole. The whole may be dimensioned in such a manner that the lumen and size of said elongated hole for guiding the needle 3 has the necessary size to accommodate the needle safely and possibly in an axially slidable manner. As stated above, other variants are also possible, e.g. one of the two ribs extending from the side walls of the groove 702 may be integral with the second part 202 of the needle-guide 2 while the other is integral with the base 102 of the needle-guide 2, or longitudinally discontinuous ribs may be provided on both parts 102, 202, alternating in such a manner as to be mutually engaged in a comb-like arrangement.

Figure 11:
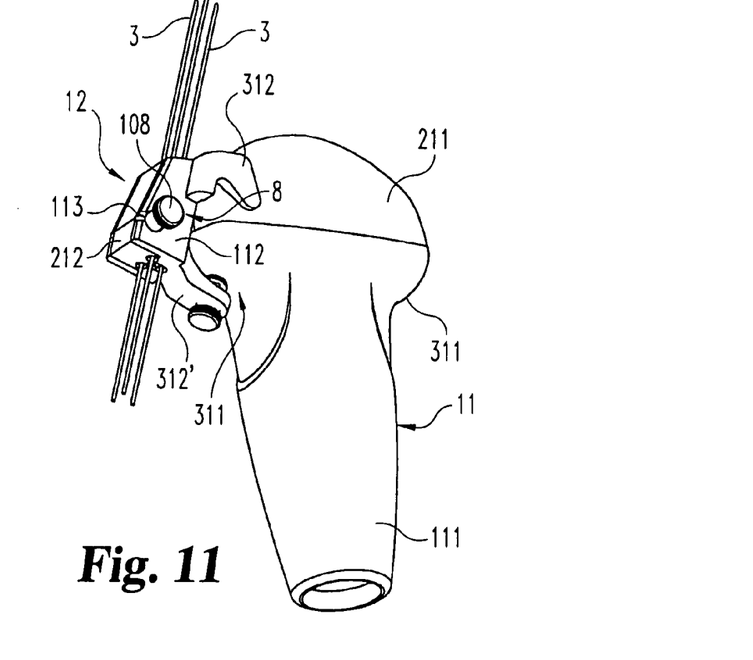
FIG. 11 is a perspective view of an additional embodiment of the probe/needle-guide combination according to the invention, particularly in which the probe is an external probe with a head shaped as a sector of a circle and wider than the handgrip.
Figure 12:
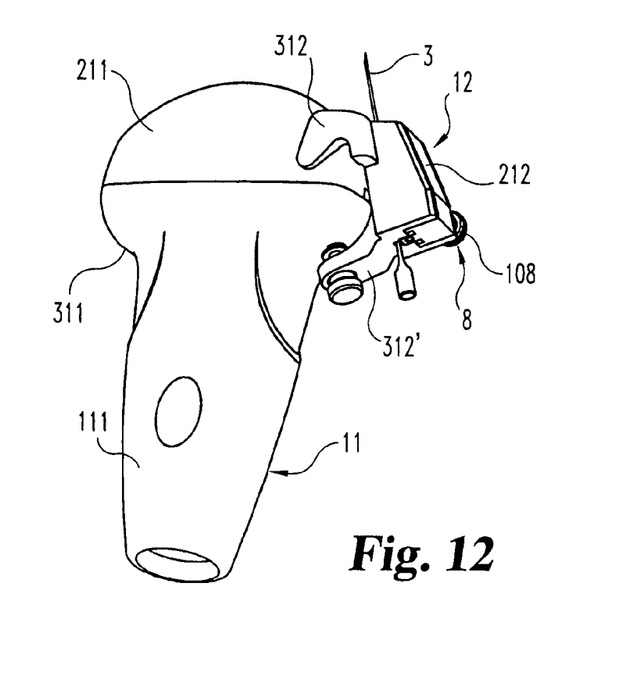
FIG. 12 is a perspective view of an additional embodiment of the probe/needle-guide combination according to the invention, particularly in which the probe is an external probe with a head shaped as a sector of a circle and wider than the handgrip.
Figure 13:
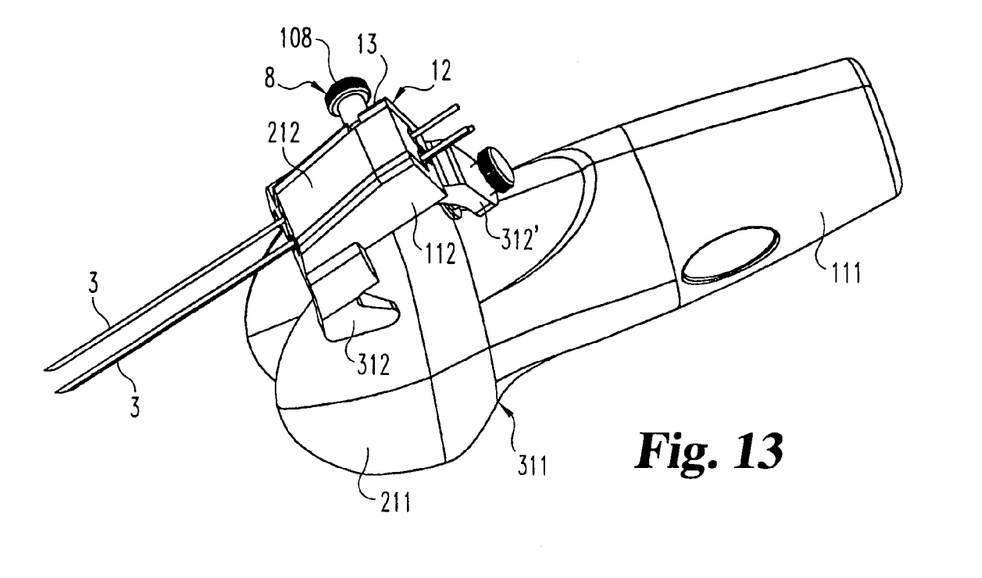
FIG. 13 is a perspective view of an additional embodiment of the probe/needle-guide combination according to the invention, particularly in which the probe is an external probe with a head shaped as a sector of a circle and wider than the handgrip.
Figure 14:
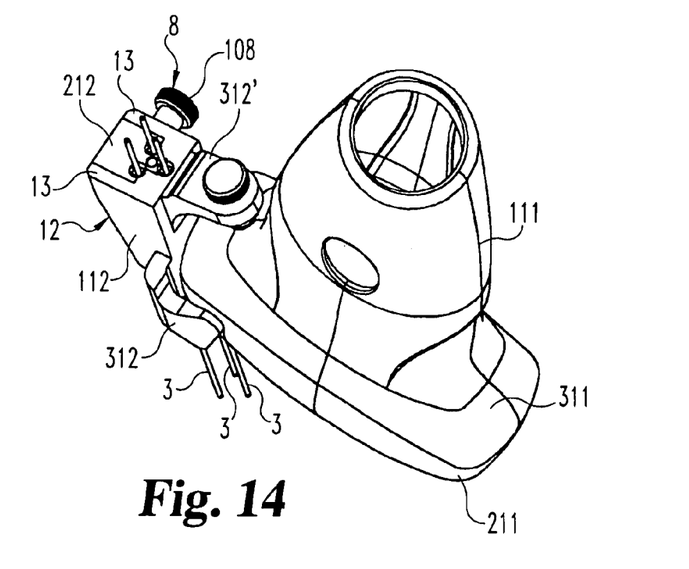
FIG. 14 is a perspective view of an additional embodiment of the probe/needle-guide combination according to the invention, particularly in which the probe is an external probe with a head shaped as a sector of a circle and wider than the handgrip.
Figure 15:
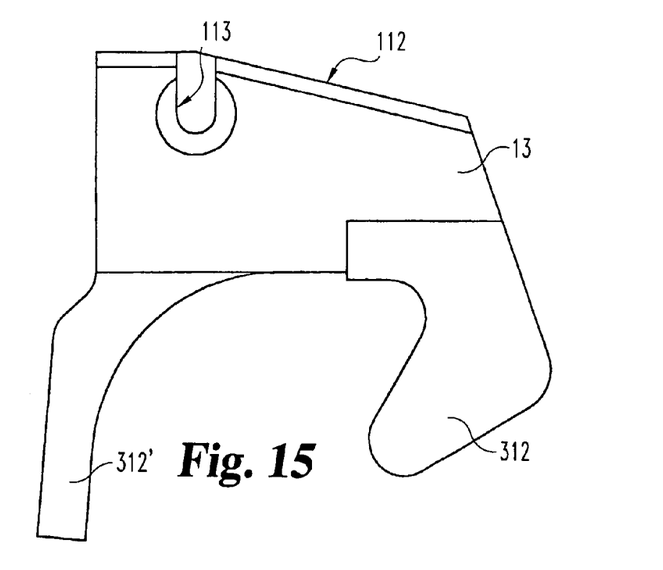
FIG. 15 is a side elevational view of the base part of the needle-guide as shown in FIGS. 11 to 14.
Figure 16:
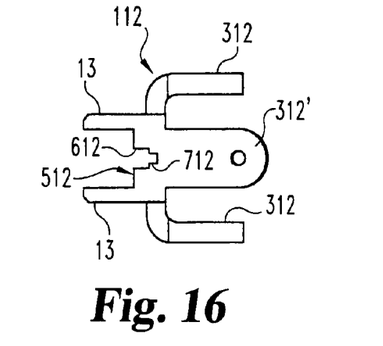
FIG. 16 is a bottom plan view of the base part of the needle-guide as shown in FIGS. 11 to 14.
Figure 17:
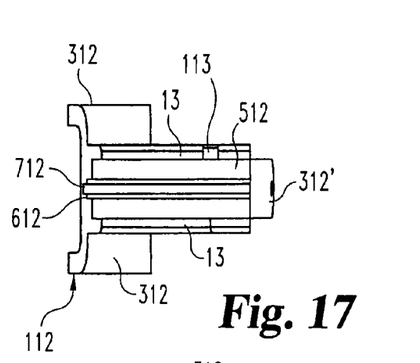
FIG. 17 is a top plan view of the base part of the needle-guide as shown in FIGS. 11 to 14.
Figure 18:
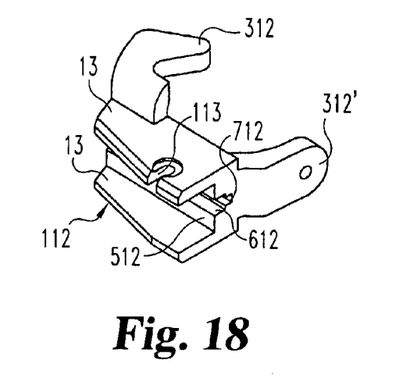
FIG. 18 is a top perspective view of the base part of the needle-guide as shown in FIGS. 11 to 14.
Figure 19:
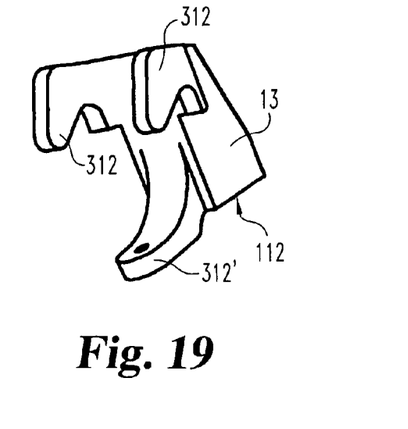
FIG. 19 is a bottom perspective view of the base part of the needle-guide as shown in FIGS. 11 to 14.

FIGS. 11 to 19 show an additional embodiment of a combination of a probe 11 and a needle-guide 12 according to the invention.

Referring to this embodiment, the probe 11 is of the type ordinarily in use for external imaging applications and has a handgrip part 111 and a widened head 211, which is curved on the front side and bulged in the direction of the axis of curvature, and forms a transverse shoulder on the rear side 311 for connection to the handgrip 111.

The needle-guide 12 is still composed of two parts, a base part 112 and a second part 212 which is removably securable to the base 112 and forms needle guiding holes therewith.

The base 112 has means for securing it to the probe 1, which consist of two lateral front wings 312 which are shaped in such a manner 11 as to adhere to the bulged portion of the case of the probe 11 in the end tapered portion thereof and on the two opposite surfaces with reference to the axis of curvature of the head of the probe 11. The base 112 has on its rear side a rear extension 312' which extends behind the shoulder 311 formed by the widened head of the probe 11, and the rear extension 312' has a threaded clamping bolt which is tightened against said shoulder 311.

Also, other connection means may be provided, not shown in the Figures, like those described in the previous embodiment, such as combinations of centering ridges and recesses over the case of the probe 11 and the base 112, as well as possible profiles of the case and of the wall of the base 112 turned toward it to define a certain orientation angle for the needles, to allow at least one of the needles 3 to be brought inside the scan area.

The needle-guide 12 is made in such a manner as to have three needle guiding holes and to be able to house three needles 3 at the same time. If the needles 3 were disposed all on the same plane, then the needle-guide 12 might have substantially the same construction as that of the needle-guide 2 of the previous embodiment.

However, in this embodiment the needles are in such a relative arrangement that their axes are coincident with the vertices of a triangle, particularly an isosceles or equilateral triangle. Therefore, the axis of one needle guiding hole is not on the same plane as the other two holes.

In order to ensure, nevertheless, that the needle guiding holes are at least partly openable on one side, by simply separating the two parts 112, 212 of the needle-guide, the separation surface has a cross section shaped like a rectangular curve.

Figure 20:
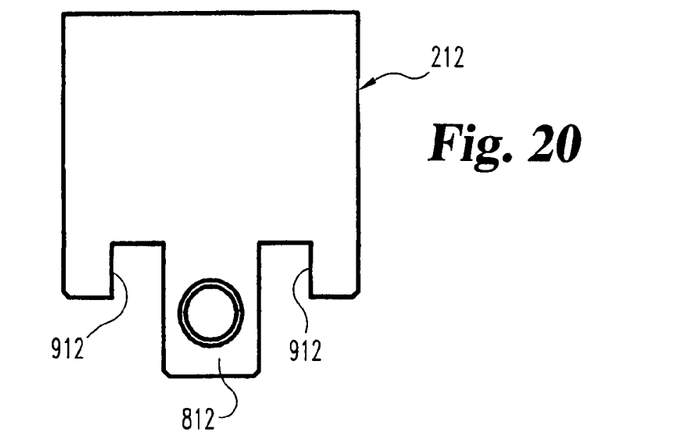
FIG. 20 is a front elevational view of the second part of the needle-guide as shown in FIGS. 11 to 14.
Figure 21:
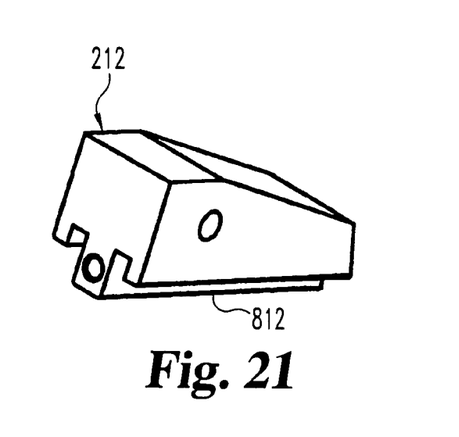
FIG. 21 is a front perspective view of the second part of the needle-guide as shown in FIGS. 11 to 14.
Figure 22:
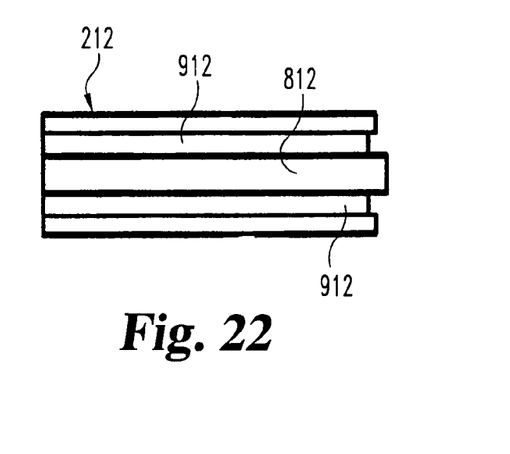
FIG. 22 is a top plan view of the second part of the needle-guide as shown in FIGS. 11 to 14.
Figure 23:
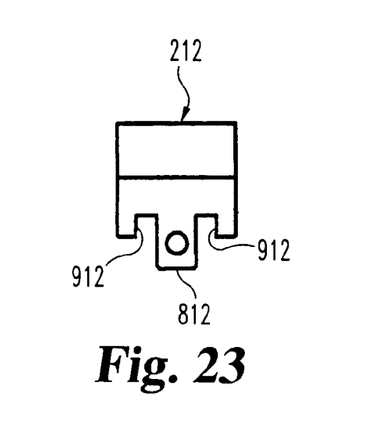
FIG. 23 is a front elevational view of the second part of the needle-guide as shown in FIGS. 11 to 14.
Figure 24:
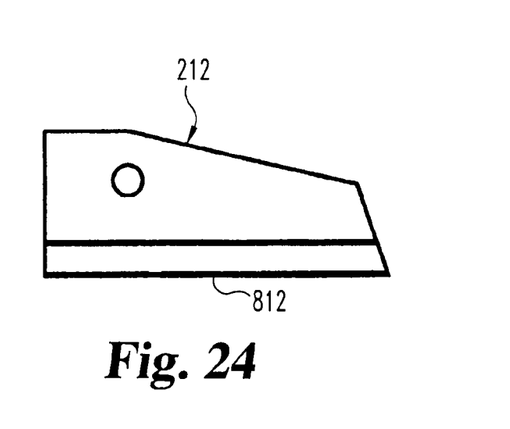
FIG. 24 is a side elevational view of the second part of the needle-guide as shown in FIGS. 11 to 14.
Figure 25:
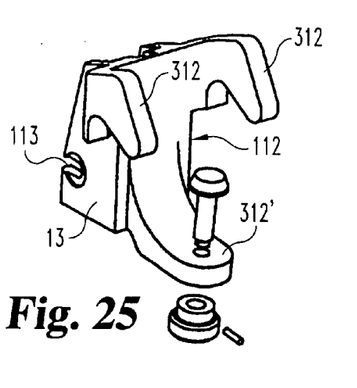
FIG. 25 is a perspective view of the needle-guide as shown in FIGS. 11 to 14.
Figure 26:
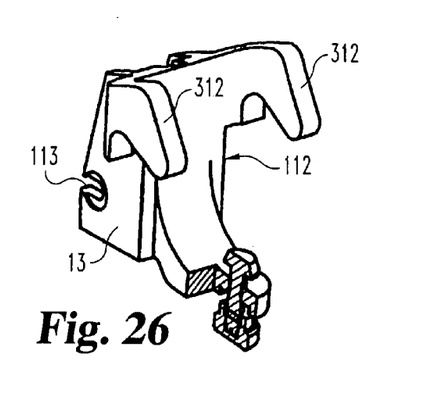
FIG. 26 is a perspective view, in partial section, of the needle-guide as shown in FIGS. 11 to 14.
Figure 27:
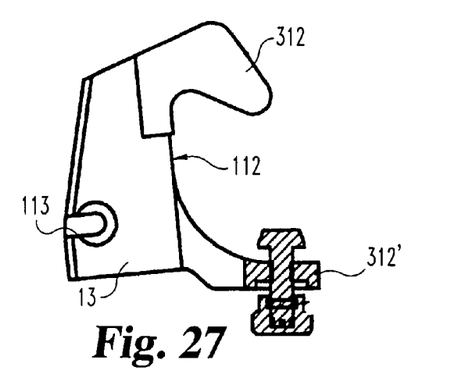
FIG. 27 is a side elevational view, in partial section, of the needle-guide as shown in FIGS. 11 to 14.
Figure 28:
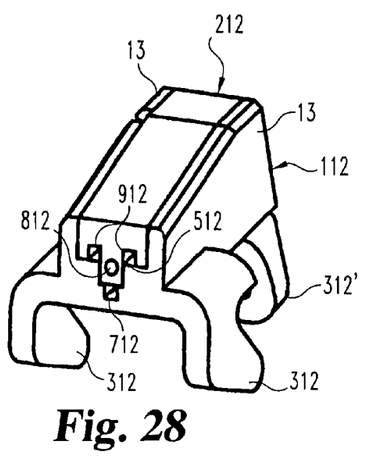
FIG. 28 is a front perspective view of the needle-guide as shown in FIGS. 11 to 14.
Figure 29:
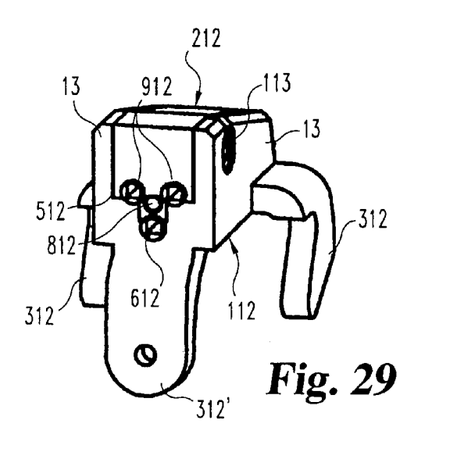
FIG. 29 is a rear perspective view of the needle-guide as shown in FIGS. 11 to 14.

The base 112 has a groove 612 in the middle position of the surface 512 for supporting the second removable part 212 of the needle-guide. In the bottom wall of said groove 612 an additional parallel groove 712 is provided, which has a proper size for the needle guiding hole, whereas the second removable part 212 of the needle-guide 12 has a rib 812 in a position coinciding with the groove 612, which engages in the groove 612 when said two parts 112, 212 are mutually connected, and forms the missing closing side of the guiding hole with the edge turned toward the inner groove 712.

The other two guiding holes are formed by two grooves 912 formed in the two abutment surfaces of the second removable part 212 against the facing surfaces of the base 112, which are disposed on the two sides of the rib 812. Said two grooves 912 have such a depth and such a width that, like the groove 712, form the two additional guiding holes, with the abutment surfaces 512 on the base part 112.

Obviously, the size of the rib 812 and of the groove 612 are such that, when said rib 812 abuts against the bottom of the groove 612, the abutment surfaces with the grooves 912 also abut against the surfaces 512 of the base part.

In the end walls of the area of the rib 812, niches or recesses 912 may be provided, for instance for gripping purposes.

As is apparent from the above, the inventive principle allows to provide different configurations of several substantially parallel needle-guiding holes, having any different position.

In order that the second removable part 212 of the needle-guide 12 may be held in position on the base 112, the latter has side walls 13 which overlap the side walls of the second part 212 of the needle-guide. The two parts may be fastened in a substantially identical, through reverted manner, with respect to the previous embodiment. One of the side walls of the second part 212 of the needle-guide has a threaded hole into which a threaded pin 8, having a widened head 108 may be screwed, whereas, in a coincident position, the corresponding side wall 12 of the base part 112 has a recess for engaging the pin which is open on the side in which said second part 212 of the needle-guide is introduced between the walls 13 of the base part 112 of the needle-guide.

Once again, in this example, the hole into which the pin is screwed may be a through hole and the side wall 13 on the side opposite to the one through which the pin 8 is screwed may have a coincident hole in which the end of the threaded pin is engaged in the same manner as in the previous embodiment when the two parts are clamped or almost clamped together.

It shall be noted that, when needed, the three-needle configuration of the needle-guide 12 may be extended without requiring any inventive activity to the endocavitary probe-specific embodiment, described with reference to FIGS. 1 to 10, the front head part of the needle-guide being easily changeable by anyone skilled in the art.

The inclination of the three needles, and their mutual position are such that one needle is situated closer to the probe and in such a position as to be able to enter the scan field thereof. The other two needles are beyond said scan field, but have a well defined and predetermined position. Particularly, the arrangement of the axes of the three needles at the vertexes of a triangle allows to easily locate the other two needles when the first is imaged upon scanning and also allows to perform a local treatment over a wider area. It shall be also noted that the provision of several needle guiding holes allows the combined use of a greater number of therapeutic and diagnostic tools, thereby allowing both a combination of therapeutic and/or surgical actions and the use of additional control probes near the therapeutic or surgical action area, to improve monitoring of the operations, both visually, by ultrasound imaging, and by detecting additional measurable parameters.

Moreover, the grooves which generate the guiding holes in combination with the facing abutment surfaces on the other part of the needle-guide 12 may be provided, for the same hole, on the one or the other of the two parts of the needle-guide and may also have extensions of the side walls, as described in the previous embodiment, any combination or subcombination of the characteristics described with reference to one embodiment with one or more characteristics or with subcombinations or with the complete combination of characteristics described with reference to the other embodiment as illustrated and described in the present disclosure being allowed.

The invention is not limited to the embodiments described and illustrated herein, but may be widely varied, especially as regards construction, without departure from the guiding principle disclosed above and claimed below. So, for example, while the needle-guides of the invention are described and shown in combined applications with ultrasound probes, they may be also used with other probes or other therapeutic or diagnostic tools.

The invention claimed is:

1. A needle-guide device for an ultrasound probe comprising a base body having means for connection to the probe and a plurality of elongated guide holes constructed and arranged to simultaneously house and guide a plurality of surgical tools, two of said plurality of surgical tools defining a first geometric plane and another of said plurality of surgical tools being disposed in a second geometric plane, wherein said first geometric plane is different from said second geometric plane, wherein said needle-guide device is made of at least two removably connectable parts, which are shaped in such a manner that each of them forms complementary parts of a peripheral delimiting wall of each of said elongated guide holes for a needle, which peripheral wall parts complete each other when said two parts of the needle-guide device are connected, thereby forming each of said elongated guide holes for guiding the needle with a 360 degree covering delimiting wall, wherein said needle-guide device is further comprised of a base part to be secured to the probe and of a removable part, a separation plane or surface being provided between the at least two parts, which is parallel to the axis of the corresponding elongated guide hole, and is secant or at least tangent to the corresponding hole, said two parts have mutual abutment surfaces and combinations of grooves and walls in the mutual abutment surfaces of said two parts which, by their mutual engagement, form the complementary parts of the surfaces delimiting each of said elongated guide holes of the needle-guide device, so that, by separating said at least two parts, all the elongated guide holes are longitudinally open on at least one portion of a side.

2. A needle-guide device for an ultrasound probe comprising a base body having means for connection to the probe and a plurality of elongated guide holes constructed and arranged to simultaneously house and guide a plurality of surgical tools, two of said plurality of surgical tools defining a first geometric plane and another of said plurality of surgical tools being disposed in a second geometric plane, wherein said first geometric plane is different from said second geometric plane, characterized in that the needle-guide device includes three elongated guide holes and the needle-guide device is divided into a base and a second part to be removably fastened to the base, the base of the needle-guide device having a surface whereby it abuts against the second part of the needle-guide device, wherein a first groove is provided in a median position, in turn having a second groove in its bottom wall, which is designed to form two longitudinal side walls and a longitudinal bottom wall of one of the elongated guide holes for one of the needles, whereas the second part of the needle-guide device has, on the surface turned toward the abutment surface of the base part, a longitudinal median rib which coincides with the longitudinal median groove in the base part and forms a missing delimiting surface of the corresponding elongated guide hole, thereby completing the delimiting surfaces formed by the second groove, whereas, in the surfaces of the second part of the needle-guide device, on the two sides of the longitudinal median rib, longitudinal grooves are provided which form, with the bands of the abutment surface of the base on both sides of the first groove, the delimiting surfaces of the two additional elongated guide holes.

3. A needle-guide device as claimed in claim 2, characterized in that the grooves which form a portion of the side walls and a wall transverse thereto for delimiting the elongated guide hole are provided partially in both opposite mutual abutment surfaces of the two parts of the needle-guide device.

4. A needle-guide device as claimed in claim 2, characterized in that the needle-guide device has a slender or tapering front head.

5. A needle-guide device as claimed in claim 4, characterized in that said front head is also perforated and is arranged to be a single piece.

6. A needle-guide device as claimed in claim 4, characterized in that the front head, which is integral with said base and the second part of the needle-guide device have complementary mutually engaging means.

7. A needle-guide device as claimed in claim 4, characterized in that at least one the through holes in said head part is widened on at least one side or for a portion of its delimiting surface inside the head, the second part of the needle-guide device having a wall extension at its end which may be axially engaged in the through hole of the front head, and which is coincident with said widened portion and complementary thereto so as to form and/or complete the delimiting wall of the through elongated guide hole, at least on a few sides.

8. A needle-guide as claimed in claim 7, characterized in that the second part of the needle-guide device has said extensions on two opposite sides and in the form of front extension wings of the two side walls of the groove provided in said second part of the needle-guide device, whereas the front head of the needle-guide device has complementary widened portions in the corresponding walls of the through hole.

9. A needle-guide device as claimed in claim 4, characterized in that an extension wing is also provided from the bottom wall of the groove of the second part of the needle-guide device, the front head of the needle-guide device being arranged to be accordingly widened at said extension wing of the bottom side of the groove of the second part of the needle-guide device.

10. A needle-guide device as claimed in claim 9, characterized in that the extension wings of the side and/or bottom walls of the groove in the second part of the needle-guide device are thinner than the wall of the second part of the needle-guide device and than the head of the needle-guide device, whereby an abutment step is formed between the front end of the second part of the needle-guide device and the facing rear end side of the front head.

11. A needle-guide device as claimed in claim 10, characterized in that the front head of the needle-guide device, which is integral with the base part of the needle-guide device, has a through aperture which communicates with the elongated guide hole provided therein at least one of the sides of said head, not coinciding with the extension wings of the second part of the needle-guide, the extension wings of the second part of the needle-guide device are meant to adhere against or turned toward the probe, whereas in the front head, the needle is only substantially guided on three sides and through less than 360° at least in coincidence with the through aperture.

12. A needle-guide device as claimed in claim 11, characterized in that the front head has a steeper tapering inclination in the portion projecting beyond the aperture on one of the sides, and that the needle projection aperture is provided in the inclined front side, and is slot-shaped due to the inclination of the front end of the head.

13. A needle-guide device as claimed in claim 4, characterized in that the length of the front head wherein each needle is guided only on a few sides is relatively small as compared with the length of the rest of the needle-guide device in which the elongated guide hole has a continuous delimiting surface.

14. A needle-guide device as claimed in claim 13, characterized in that the front head has needle guiding surfaces covering less than 360° and wherein the missing delimiting surface is alternated in different positions through successive sectors of the head.

15. A needle-guide device as claimed in claim 12, characterized in that, at the more tapered front end, the elongated guide hole delimiting walls are continuous and made of one piece, as well as directly accessible from the aperture wherefrom a needle projects.

* * * * *